United States Patent [19]
Pawellek et al.

[11] 3,978,131
[45] Aug. 31, 1976

[54] PROCESS FOR PREPARING 4-AMINO-DIPHENYLAMINE

[75] Inventors: Dieter Pawellek; Edmund Bielendorfer, both of Leverkusen; Karlfried Wedemeyer, Cologne, all of Germany

[73] Assignee: Bayer Aktiengesellschaft, Leverkusen, Germany

[22] Filed: Oct. 22, 1974

[21] Appl. No.: 516,946

[30] Foreign Application Priority Data
Nov. 8, 1973  Germany............................ 2355737

[52] U.S. Cl. .............................................. 260/576
[51] Int. Cl.² ......................................... C07C 85/02
[58] Field of Search.................. 260/576; 252/477 A

[56] References Cited
UNITED STATES PATENTS

| | | |
|---|---|---|
| 2,813,124 | 11/1957 | Rice et al............................ 260/576 |
| 2,822,395 | 2/1958 | Dent................................... 260/576 |
| 2,974,169 | 3/1961 | Newby................................ 260/576 |
| 3,055,940 | 9/1962 | Merz................................... 260/576 |
| 3,281,470 | 10/1966 | Vertnik............................. 260/576 X |
| 3,781,227 | 12/1973 | Sokolsh et al. ............. 260/447 Q X |

FOREIGN PATENTS OR APPLICATIONS 168,711   3/1964   U.S.S.R............................. 260/576

*Primary Examiner*—Allen B. Curtis
*Attorney, Agent, or Firm*—Burgess, Dinklage & Sprung

[57] ABSTRACT 4-amino-diphenylamine is prepared by catalytically hydrogenating 4-nitroso-diphenylamine in a water-immiscible solvent in the presence of Raney nickel as a catalyst. The hydrogenation reaction is generally carried out at a temperature in the range of from 20° to 150°C and can be carried out under an elevated hydrogen pressure of up to 50 atmospheres.

9 Claims, No Drawings

PROCESS FOR PREPARING 4-AMINO-DIPHENYLAMINE

BACKGROUND

This invention relates to a process for the catalytic hydrogenation of 4-nitroso-diphenylamine to form 4-amino diphenylamine.

It is already known that 4-nitroso-diphenylamine can be hydrogenated in isopropanol in the presence of a palladium-carbon catalyst (British Pat. No. 935,303). It is also known that the potassium or sodium salt of 4-nitroso-diphenylamine can be hydrogenated in an aqueous solution using palladium or platinum catalysts in conjunction with benzene (German Pat. No. 1,266,766). It is also known that a 2-component catalyst containing nickel and manganese can be used for catalytic hydrogenation in aqueous solution (DOS No. 1,941,008). However, the use of Raney nickel as a catalyst in the catalytic hydrogenation of 4-nitroso-diphenylamine is not known.

SUMMARY

It has now been found that high yields of extremely pure 4-amino-diphenylamine can be obtained by catalytically hydrogenating 4-nitroso diphenylamine, providing the 4-nitroso-diphenylamine is hydrogenated in a water-immiscible solvent in the presence of Raney nickel as a catalyst. The hydrogenation temperature can be varied within wide limits. In general, hydrogenation is carried out at a temperature of from 20° to 150°C. The temperature is preferably kept between 60° and 120°C and, more particularly, between 90° and 110°C.

DESCRIPTION

Although hydrogenation can be carried out under normal pressure, shorter reaction times are generally required where higher hydrogen pressures are applied. Accordingly, it is advantageous to work under a hydrogen pressure of 3 to 50 atms., preferably in the range of from 5 to 20 atms., and, more particularly, in the range of from 10 to 16 atms.

Examples of water-immiscible solvents suitable for use in the process according to the invention include aromatic hydrocarbons such as benzene, toluene and xylene.

Aromatic amines can be used with advantage as water-immiscible solvents.

Particularly preferred water-immiscible solvents are aniline and its derivatives, such as the corresponding toluidines xylidines and their derivatives monoalkylated or dialkylated on the nitrogen atom.

Particularly suitable water-immiscible solvents are aniline, N-methyl-aniline, N,N-dimethyl-aniline, 2-methyl-, 3-methyl- and 4-methyl-aniline and 2,4-xylidine and 2,6-xylidine.

Mixtures of the aforementioned solvents can, of course, also be used.

The quantity in which the solvent is used is selected in such a way that a solution of the 4-nitroso-diphenylamine is formed. The quantity required for this purpose is governed by the particular solvent used and by the temperature of the solution. An excess beyond this minimum necessary quantity is not critical and, in some cases, can be advantageous. In general, however, the excess of solvent should not be too great and can be limited with advantage to about three times and, more especially, to about 1.5 times the necessary quantity. In general, the quantity of solvent used in the process according to the invention at room temperature is up to 27 ml, preferably up to 20 ml and, more particularly, about 13.5 ml per g of 4-nitroso-diphenylamine.

For example, a substantially saturated solution of 4-nitroso-diphenylamine containing 8, 20 and 50% by weight of 4-nitroso-diphenylamine is obtained at room temperature using about 13 ml, 5 ml and 1.2 ml of aniline per g of 4-nitroso-diphenylamine. Accordingly, it can be advantageous to prepare the 4-nitroso-diphenylamine solution at a temperature higher than room temperature, thereby reducing the quantity of solvent required.

Although the presence of water in the 4-nitroso-diphenylamine solution is not critical in the process according to the invention, it is advantageous when preparing the solution to ensure that a second, aqueous phase is not formed as a result of the solubility limit for water being exceeded. Should this be the case, it can readily be separated off by conventional methods. Alternatively, the water content of the solution can be reduced by azeotropic distillation of the water with an excess of the solvent or solvent mixture.

In cases where a moist water-containing 4-nitroso-diphenylamine is used, it is also possible advantageously to use a relatively large excess of the solvent or solvent mixture and to remove both that part of the water which is not soluble in the solution and also a fraction of the water dissolved in the solution by azeotropic distillation with part of the excess solvent or solvent mixture.

Similarly, it can be particularly advantageous to react the 4-nitroso-diphenylamine in the form of its hydrochloride with the requisite quantity of a base, for example sodium or portassium hydroxide, in aqueous solution in the presence of an excess of the solvent used, and to extract the 4-nitroso-diphenylamine liberated with the solvent. After the aqueous alkali chloride solution has been separated off, the water can be removed with particular advantage by azeotropic distillation and the solution can be adjusted to the requisite concentration in the same distillation stage.

4-Nitroso-diphenylamine is prepared by known methods, for example by rearrangement of N-nitroso-diphenylamine in the presence of alcoholic hydrochloric acid. The 4-nitroso-diphenylamine accumulates in the form of its hydrochloride. In the procedure adopted, the 4-nitroso-diphenylamine hydrochloride is preferably prevented from crystallising out by selecting the reaction conditions in such a way that the hydrochloride of the 4-nitroso-diphenylamine remains dissolved in the reaction medium. The solution is then run with thorough stirring into excess, aqueous alkali, for example sodium hydroxide, and the aqueous solution is adjusted to a pH-value of from 7 to 11 by the addition of, for example, hydrochloric acid. The 4-nitroso-diphenylamine thus precipitated can then be isolated by known methods and washed with water until free from salts and methanol. It is advisable to remove most of the alcohol, for example methanol, in carrying out the process according to the invention.

In the case described above, the 4-nitroso-diphenylamine precipitated can advantageously be directly dissolved in an excess of the solvent or solvent mixture used. The aqueous phase containing the salts and alcohol can then be separated off and the solution of the 4-nitroso-diphenylamine subsequently freed from alcohol and water by azeotropic distillation.

The absence of alcohol, especially methanol, is preferable in the process according to the invention, because undersirable secondary products accumulate where methanol is present during hydrogenation. Thus, the purity of a distilled 4-amino-diphenylamine, prepared in the presence of methanol, only amounts to between 97 and 98% according to analysis by gas chromatography, because 1.2 to 1.4% of diphenylamine and 0.6 to 0.9% of an unknown compound have also been formed. It is only possible to separate these two compounds from the 4-amino-diphenylamine by complicated, high-loss fractional distillation.

On the other hand, a 4-nitroso-diphenylamine hydrochloride obtained in alcoholic solution can also be freed from the alcohol adhering to it, for example methanol, by washing it with one of the water-immiscible solvents according to the invention, for example benzene or toluene, and subsequently dissolving the moist product in the solvent selected for carrying out the process according to the invention.

In general, the process according to the invention can be carried out by dissolving the 4-nitroso-diphenylamine in the solvent used, adding the selected quantity of Raney nickel as catalyst and hydrogenating the solution at the pressure selected.

The reaction time required for this purpose is governed by the quantity and concentration of the solution and catalyst, by the reaction temperature and by the hydrogen pressure selected. Accordingly, it is not possible to quote a reaction time applicable to every case, and the reaction time can actually vary between a few minutes and a few hours.

On completion of the reaction, the catalyst is separated off in known manner, for example by filtration or centrifuging. The reaction product is subsequently isolated from the catalyst-free solution in known manner, for example by distillation or crystallisation.

The process according to the invention can be carried out with particular advantage immediately after preparation of the 4-nitroso-diphenylamine hydrochloride. The particular water-immiscible solvent selected is added to the aqueous alcoholic acid solution of the 4-nitroso diphenylamine hydrochloride as it accumulates during preparation. The 4-nitroso-diphenylamine is subsequently liberated by adding the requisite quantity of alkali, for example sodium hydroxide, and simultaneously dissolved in the solvent. The now neutral to weakly alkaline salt-containing aqueous alcoholic phase is separated off. The residual organic solution of the 4-nitroso-diphenylamine is then freed from the adhering and dissolved water and alcohol by distillation, followed by concentration to the required level.

The aforementioned distillation stage for removing water and/or alcohol and for concentrating the solution can be carried out either under normal pressure or under reduced pressure. The pressure is not an important factor, and with advantage is selected according to the possibilities available. Naturally, shorter distillation times and/or a lower heat input are required at reduced pressures.

The process according to the invention has significant advantages. Raney nickel is a readily commercial catalyst which does not undergo any reduction in activity even in the event of repeated or continuous use. The 4-nitroso-diphenylamine hydrochloride accumulating during the commercial production of 4-nitroso-diphenylamine may optionally be directly converted particularly easily in the described manner into the solution according to the invention, thereby eliminating the need for complicated isolation and purification. The reaction according to the invention is highly selective and enables the end product to be readily isolated without any need for complicated measures, simply by distilling off the solvent used which may be reused, optionally without further purification. The purity of the 4-amino diphenylamine is so high that it can be used as an intermediate product for further reactions without any need for further purification. The diphenylamine content is minimal. Straightforward distillation may optionally be carried out for purification, the distillation residue generally remaining liquid at temperatures above 100°C. The residue can readily be eliminated without polluting the environment, for example by burning.

The process according to the invention can, of course, also be carried out continuously. In that case, the particular measures required, such as dissolving the 4-nitroso-diphenylamine or extracting the 4-nitroso-diphenylamine from an aqueous or aqueous-alcoholic acid solution of the 4-nitroso-diphenylamine hydrochloride, following addition of the requisite quantity of alkali, by a water-immiscible solvent, removing water and, optionally, methanol or another lower alcohol from the organic solution of the 4-nitroso-diphenylamine by azeotropic distillation, concentrating the solution, adding the catalyst, catalytic hydrogenation, separating off the catalyst, distilling off the solvent and distilling the reaction product obtained, can all be carried out in known manner.

4-Amino-diphenylamine is a known intermediate product for antiagers and antioxidants (U.S. Pat. No. 2,041,782; Ullmanns Enzyklopadie der Technischen Chemie, 3rd Edition, Vol. 13, page 491 (1962)).

The following Examples illustrate the invention.

EXAMPLE 1

A suspension of 117 g (0.5 mol) of 4-nitroso-diphenylamine hydrochloride in 250 ml of toluene is stirred with 800 ml of aniline at 25°C, the pH-value rising from below 1 to between 3.5 and 4.0. A 10% by weight aqueous sodium hydroxide solution is then run in until the pH-value reaches 6, after which the pH-value is adjusted to between 10.5 and 11.0 by the dropwise addition of more sodium hydroxide. After the stirrer has been switched off, the dark-coloured organic phase quickly separates from the pale yellow coloured, clear aqueous layer. The organic phase is separated off and predistilled under a pressure of 50 Torr up to a boiling temperature of 50°C, and water is thereby removed in the form of a water-toluene azeotrope. The solution, containing approximately 9% by weight of 4-nitroso-diphenylamine, is subsequently transferred to a 5000 ml capacity stirrer-equipped autoclave, and 10 g of aniline-moist Raney nickel which has been stored under aniline are added to it, followed by hydrogenation at 100°C/16 atms. After a reaction time of about 10 minutes, the theoretically necessary quantity of hydrogen has been taken up, and the autoclave is cooled and vented. The catalyst is filtered off and washed with aniline. The filtrate and washing liquid (aniline) are combined and concentrated by distillation under reduced pressure (20 Torr). The distillation residue is distilled, giving 83 g (90% of the theoretical amount) of 4-amino-diphenylamine boiling at 167°–177°C/0.7 Torr with a purity of 99.8% (according to analysis by gas chromatography).

The catalyst filtered off, which is kept anilinemoist, is used another three times in the same way as described above in repetitions of the Example. The reaction time elapsing before the theoretically necessary quantity of hydrogen was taken up amounted to 10, 11 and 10 minutes. The yields of distilled, more than 99% pure 4-amino-diphenylamine amounted to 81 g, 82 and 83 g, corresponding to 88, 89 and 90% of the theoretical amount.

EXAMPLE 2

A solution of 4-nitroso-diphenylamine in aniline/toluene with a pH-value of 10.5 to 11.0 was prepared in the same way as described in Example 1. This solution was transferred immediately, i.e., without azeotropic distillation, to a 5000 ml stirrer-equipped autoclave, and 10 g of aniline-moist Raney nickel which had been stored under aniline, were added to it, followed by hydrogenation at 100°C/16 atms. hydrogen pressure. The reaction time elapsing before the theoretically necessary quantity of hydrogen was taken up amounted to 140 minutes. Working up of the reaction mixture in the same way as described in Example 1 produced 77 g (83% of the theoretical yield) of 4-amino-diphenylamine with a purity of 98.4% (according to analysis by gas chromatography).

EXAMPLE 3

A solution of 4-nitroso-diphenylamine in toluene/aniline prepared as described in Example 1 and freed from water by azeotropic distillation is hydrogenated at 100°C/16 atms. hydrogen pressure with water-moist Raney nickel which had been stored under water. The reaction time required for taking up the theoretically necessary quantity of hydrogen amounted to 98 minutes. The reaction mixture was worked up as described in Example 1, giving 83 g (90 percent of the theoretical yield) of 4-amino diphenylamine with a purity of 99 percent (according to analysis by gas chromatography).

EXAMPLE 4

A solution of 4-nitroso diphenylamine in toluene/aniline was prepared as described in Example 1 and concentrated by distillation to a 4-nitroso-diphenylamine content of 20% by weight. The resulting water-free and toluene-free aniline solution of the 4-nitroso-diphenylamine (500 ml) was hydrogenated at 100°C/16 atms. hydrogen pressure in a 700 ml capacity stirrer-equipped autoclave, following the addition of 10 g of aniline-moist Raney nickel which had been stored under aniline. The theoretically necessary quantity of hydrogen had been taken up after 52 minutes. The reaction mixture was worked up in the same way as described in Example 1, giving 82 g (90 percent of the theoretical yield) of 4-amino-diphenylamine with a purity of 98 percent (according to analysis by gas chromatography).

EXAMPLE 5

A solution of 4-nitroso-diphenylamine in toluene/aniline was prepared as described in Example 1 and subsequently concentrated by distillation to a 4-nitroso-diphenylamine content of 40% by weight. The resulting solution (250 ml) was hydrogenated at 100°C/16 atms. hydrogen pressure in a 700 ml capacity stirrer-equipped autoclave following the addition of 10 g of aniline-moist Raney nickel which had been stored under aniline. The theoretically necessary quantiy of hydrogen had been taken up after 60 minutes. The reaction mixture was worked up as described in Example 1, giving 81 g (88 percent of the theoretical yield) of 4-amino-diphenylamine with a purity of 98.5 percent (according to analysis by gas chromatography).

EXAMPLE 6

A suspension of 117 g (0.5 mol) of 4-nitroso-diphenylamine hydrochloride in 250 ml of toluene is stirred at 50°C with 400 ml of aniline. At the same time, 10% by weight aqueous sodium hydroxide solution is run in until a pH-value of 6 is reached, after which the pH-value is adjusted to between 10.5 and 11.0 by dropwise addition of the sodium hydroxide, the temperature being maintained at 50°C. After the stirrer has been switched off, the dark-coloured organic phase quickly separates from the pale yellow coloured, clear aqueous layer. The organic phase is separated off and, by distillation under a reduced pressure of 50 Torr up to a boiling point of 50°C, is freed from water which distills over in the form of a water-toluene azeotrope. Toluene is then distilled off under a reduced pressure of 20 Torr at a boiling temperature of about 80° to about 85°C, and the solution is concentrated to a 4-nitroso-diphenylamine content of 20% by weight. Hydrogenation is carried out at 100°C/16 atms. hydrogen pressure following the addition of 10 g of aniline-moist Raney nickel which had been stored under aniline. The theoretically necessary quantity of hydrogen is absorbed after 57 minutes. 4-Amino-diphenylamine is obtained in a yield of 81 g (88 percent of the theoretical yield), purity 98.5 percent (according to analysis by gas chromatography).

EXAMPLE 7

In a 3 litre stirrer-equipped vessel, 800 ml of aniline are added to a solution of 99 g (0.5 mol) of 4-nitroso-diphenylamine, 82 g of sodium chloride and 31 g of sodium hydroxide in 613 g of water and 321 g of methanol (= 1160 ml), followed by the addition with stirring of 10% aqueous hydrochloric acid until a pH-value of about 10.5 to 11.0 has been reached. After the stirrer has been switched off, the dark coloured organic phase quickly separates from the pale yellow coloured, clear aqueous layer. The organic phase is distilled and, hence, methanol and water together with some of the aniline are removed until the volume of the distillation solution only amounts to 500 ml (= 499 g) and the 4-nitroso-diphenylamine content has risen to 20% by weight. This solution is then transferred to a 700 ml capacity stirrer-equipped autoclave, followed by the addition of 10 g of Raney nickel which had been stored under aniline, after which the solution is hydrogenated at 100°C/16 atms. hydrogen pressure. The theoretically necessary quantity of hydrogen is taken up after 11 minutes. 4-Amino-diphenylamine is obtained in a yield of 82 g (89 percent of the theoretical amount), purity 98.5 percent (according to analysis by gas chromatography).

EXAMPLE 8

In a 3-litre stirrer-equipped vessel, 10% aqueous hydrochloric acid is slowly added with stirring to a solution of 99 g (0.5 mol) of 4-nitroso-diphenylamine, 82 g of sodium chloride and 31 g of sodium hydroxide in 321 g of methanol and 613 g of water (= 1160 ml), until a Ph-value of 10.5 to 11.0 has been reached. The free 4-nitroso-diphenylamine precipitated is then filtered under suction and washed with 700 ml of water so that the filter cake is substantially free from methanol. The 140 g filter cake containing approximately 40% by weight of water is then dissolved in 800 ml of aniline, in which it is completely soluble. The dark brown solution obtained is concentrated under reduced pressure (15 Torr) to 500 ml, the water present in the filter cake distilling off azeotropically with the aniline.

The aniline solution now containing 20% by weight of 4-nitroso-diphenylamine is transferred to a 700 ml stirrer-equipped autoclave, 10 g of aniline-moist Raney nickel which has been stored under aniline are added and the solution is hydrogenated at 100°C/16 atms. hydrogen pressure. The theoretically necessary quantity of hydrogen is taken up after 40 minutes. 4-Amino-diphenylamine is obtained in a yield of 85 g (90.5 percent of the theoretical amount), purity 98.5 percent (according to analysis by gas chromatography).

EXAMPLE 9

A suspension of 117 g (0.5 mol) of 4-nitroso-diphenylamine hydrochloride in 250 ml of toluene is stirred at 25°C with 800 ml of the solvents quoted in the following Table. The pH-value of the aqueous solution is adjusted to 10.5 – 11.0 by adding a 10% by weight aqueous sodium hydroxide solution. After the stirrer has been switched off, the phases quickly separate and the organic phase is run off and concentrated under a pressure of 50 Torr until a volume of 400 ml has been reached. This 400 ml solution is hydrogenated at 100°C/16 atms. hydrogen pressure with 10 g of water-moist Raney nickel as catalyst in a 700 ml capacity stirrer-equipped autoclave. After the theoretically necessary quantity of hydrogen has been taken up, the mixture is allowed to cool and the autoclave is vented. The catalyst is filtered off and the reaction mixture is analysed by gas chromatography. The quantity of reaction solution obtained, its analysis by gas chromatography and the yield calculated therefrom as a percentage of the theoretical yield and in g are shown in the following Table.

EXAMPLE 10

An aniline-toluene solution containing about 9% by weight of 4-nitroso-diphenylamine, prepared in accordance with Example 1 and dehydrated by azeotropic distillation, was hydrogenated at 150°C/10 atms. hydrogen pressure in the presence of about 10 g of aniline-moist Raney nickel which had been stored under aniline. After about 10 minutes, the theoretically necessary quantity of hydrogen had been taken up and the reaction product was worked up in the same way as described in Example 1. 81 g (88 percent of the theoretical yield) of 4-amino-diphenylamine were obtained with a purity of 98 percent (according to analysis by gas chromatography).

When the procedure described above was repeated with a hydrogen pressure of only 6 atms., the theoretically necessary quantity of hydrogen was taken up over a period of 5 hours. The quantity and purity of the 4-amino diphenylamine obtained were the same.

EXAMPLE 11

An aniline-toluene solution containing approximately 9% by weight of 4-nitroso-diphenylamine, prepared as described in Example 1 and dehydrated by azeotropic distillation, was hydrogenated at 80°C/50 atms. hydrogen pressure in the presence of aniline-moist Raney nickel which had been stored under aniline. The theoretically necessary quantity of hydrogen had been taken up after 9 minutes. The reaction mixture was worked up as described in Example 1, giving 76 g (82 percent of the theoretical yield) of 4-amino-diphenylamine with a purity of 98 percent (according to analysis by gas chromatography).

What is claimed is:

1. Process for preparing 4-amino-diphenylamine which comprises hydrogenating 4-nitroso-diphenylamine dissolved in a water-immiscible solvent selected from the group of aniline, the toluidines, xylidines and their derivatives monoalkylated or dialkylated on the nitrogen atom and mixtures thereof in absence of a second, aqueous phase and in the presence of Raney nickel as a catalyst.

2. Process of claim 1 wherein hydrogenation is carried out at a temperature in the range of from 20° to 150°C.

3. Process of claim 2 wherein the temperature is from 60° to 120°C.

4. Process of claim 2 wherein the temperature is from 90° to 110°C.

5. Process of claim 1 wherein hydrogenation is carried out under an elevated hydrogen pressure of up to 50 atmospheres.

| Solvent Type | Density | Reaction product | | | yield 4-amino diphenylamine | |
|---|---|---|---|---|---|---|
| | | quantity g | gas-chromatographic analysis solvent % | others % | g | % of the theoretical |
| N-methyl aniline | 0.986 | 486 | 81.8 | 1.2 | 17.0 | 82.8 | 90 |
| N,N-dimethyl aniline | 0.956 | 476 | 80.9 | 1.3 | 17.8 | 84.6 | 92 |
| 2-methyl aniline | 1.004 | 492 | 81.7 | 0.5 | 17.8 | 87.5 | 94 |
| 3-methyl aniline | 0.989 | 487 | 82.0 | 0.8 | 17.2 | 83.7 | 91 |
| 4-methyl aniline | 1.046 | 494 | 81.9 | 1.4 | 16.7 | 82.8 | 90 |
| xylidine mixture | 0.980 | 484 | 81.9 | 0.8 | 17.3 | 83.7 | 91 |

6. Process of claim 5 wherein the pressure is 5 to 20 atmoshperes.

7. Process of claim 5 wherein the pressure is from 10 to 16 atmospheres.

8. Process of claim 1 wherein the water-immiscible solvent additionally contains an aromatic hydrocarbon, 9. Process of claim 8 wherein the aromatic hydrocarbon is benzene, toluene or xylene.

* * * * *